US009528952B1

(12) United States Patent
Heibel

(10) Patent No.: US 9,528,952 B1
(45) Date of Patent: Dec. 27, 2016

(54) PULSED NEUTRON GENERATED PROMPT GAMMA EMISSION MEASUREMENT SYSTEM FOR SURFACE DEFECT DETECTION AND ANALYSIS

(71) Applicant: Westinghouse Electric Company LLC, Cranberry Township, PA (US)

(72) Inventor: Michael D. Heibel, Harrison City, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 0 days.

(21) Appl. No.: 15/156,757

(22) Filed: May 17, 2016

(51) Int. Cl.
*G01T 3/00* (2006.01)
*G01N 23/222* (2006.01)

(52) U.S. Cl.
CPC ................... *G01N 23/222* (2013.01)

(58) Field of Classification Search
CPC .... G01N 23/203; G01N 23/222; G01N 29/22; G01N 33/383
USPC .......................................................... 250/391
See application file for complete search history.

(56) References Cited

U.S. PATENT DOCUMENTS

| | | | | |
|---|---|---|---|---|
| 3,025,399 A * | 3/1962 | Verbinski | ............. | G01N 23/222 250/302 |
| 4,121,098 A * | 10/1978 | Jagoutz | ................ | G01N 23/223 250/336.1 |
| 4,293,767 A * | 10/1981 | Fischer | ................ | G01N 23/203 250/308 |
| 4,331,871 A * | 5/1982 | Allinikov | ............ | G01N 21/91 250/302 |
| 4,400,621 A * | 8/1983 | Kiefer | ...................... | G01T 1/38 250/374 |
| 4,870,669 A * | 9/1989 | Anghaie | ................ | G01N 23/18 378/58 |
| 5,731,567 A * | 3/1998 | Kato | ..................... | B23K 9/0026 219/136 |
| 5,742,061 A * | 4/1998 | Lemonnier | ............. | H01J 47/06 250/374 |
| 5,781,602 A * | 7/1998 | Fero | ....................... | B23K 31/12 376/159 |
| 5,795,712 A * | 8/1998 | Beriozkina | ............ | G01N 21/91 252/408.1 |
| 5,940,460 A * | 8/1999 | Seidel | ...................... | G01T 3/08 250/370.01 |
| 6,157,699 A * | 12/2000 | Dunn | ..................... | G01N 23/20 378/58 |
| 7,430,479 B1 * | 9/2008 | Holslin | ................... | G01T 1/167 250/359.1 |
| 2003/0001120 A1 * | 1/2003 | Nishiyama | ........... | G01N 21/274 250/559.45 |

(Continued)

OTHER PUBLICATIONS

Author: G. Jennings et al., Title: Novel Compact Accelerator-Based Neutron and Gamma Sources for Future Detector Calibration, Date: 2013, Publisher: Snowmass 2013 White Paper.*

*Primary Examiner* — David J Makiya
*Assistant Examiner* — Taeho Jo
(74) *Attorney, Agent, or Firm* — Joseph C. Spadacene; Westinghouse Electric Company LLC

(57) ABSTRACT

A method of determining structural defects in a component that utilizes neutron activation of a solution having the ability to penetrate small cracks on the surface of a material via capillary absorption that produces a discernable prompt gamma release of a defined energy when exposed to a neutron pulse. The intensity of the gamma rays produced at the desired energy at a user controlled position on the surface is used to determine the crack location, length and depth.

20 Claims, 2 Drawing Sheets

(56) References Cited

U.S. PATENT DOCUMENTS

| | | | | |
|---|---|---|---|---|
| 2003/0165213 A1* | 9/2003 | Maglich | G01N 23/222 | 376/159 |
| 2005/0117682 A1* | 6/2005 | Akers | G01N 23/066 | 376/157 |
| 2005/0220247 A1* | 10/2005 | Ruddy | G01V 5/0091 | 376/159 |
| 2007/0108973 A1* | 5/2007 | Lanning | B82Y 25/00 | 324/240 |
| 2008/0231734 A1* | 9/2008 | Enomoto | H04N 1/401 | 348/246 |
| 2009/0175401 A1* | 7/2009 | Bertozzi | G01T 3/00 | 376/154 |
| 2010/0109659 A1* | 5/2010 | Chang | G01N 27/9026 | 324/240 |
| 2011/0144952 A1* | 6/2011 | Zaidi | G06F 19/3481 | 702/189 |
| 2011/0233418 A1* | 9/2011 | Horsfall | G01T 1/241 | 250/370.14 |
| 2012/0002788 A1* | 1/2012 | Yang | G01V 5/0025 | 378/88 |
| 2012/0155592 A1* | 6/2012 | Gozani | G01T 3/06 | 376/154 |
| 2012/0199754 A1* | 8/2012 | Nose | G01N 23/222 | 250/393 |
| 2012/0207271 A1* | 8/2012 | Yang | G01V 5/0016 | 378/54 |
| 2012/0326043 A1* | 12/2012 | Duraj | G01T 3/06 | 250/362 |
| 2012/0330570 A1* | 12/2012 | Hedl | G01N 29/043 | 702/39 |
| 2013/0112885 A1* | 5/2013 | Takahashi | C09K 11/7734 | 250/367 |
| 2013/0208843 A1* | 8/2013 | Mauerhofer | G01N 23/222 | 376/159 |
| 2013/0261876 A1* | 10/2013 | Froom | B64F 5/0045 | 701/29.3 |
| 2013/0285068 A1* | 10/2013 | Heibel | H01L 31/118 | 257/77 |
| 2015/0063903 A1* | 3/2015 | Matthews | B23P 6/00 | 403/267 |
| 2015/0323473 A1* | 11/2015 | Mitra | G01T 3/00 | 250/390.04 |
| 2015/0377803 A1* | 12/2015 | Turner | G01N 23/203 | 378/41 |
| 2016/0194558 A1* | 7/2016 | Riddle | G01T 1/16 | 250/390.11 |

* cited by examiner

PULSED NEUTRON GENERATED PROMPT GAMMA EMISSION MEASUREMENT SYSTEM FOR SURFACE DEFECT DETECTION AND ANALYSIS

BACKGROUND

1. Field

This invention relates in general to the detection of cracks in irradiated surfaces and, more particularly, the nondestructive examination of irradiated components to determine structural flaws.

2. Related Art

In the event highly radioactive components or the containers of radioactive materials need to be manipulated, it is important to ensure the structural integrity of the components or material containers be assessed to minimize the potential for loss of control and containment of the radioactive material. The structural integrity of radioactive components or containers of radioactive materials resident in high radiation fields is difficult to assess using standard visual and ultrasonic Non-Destructive Examination (NDE) techniques due to the impact the radiation field has on equipment access and operability. A need exists to provide a means to evaluate the structural integrity of radioactive components and containers of radioactive materials using methodology and devices suitable for a high radiation environment.

SUMMARY

This invention discloses a method of nondestructively detecting structural defects in a surface of an irradiated material comprising the step of applying a liquid crack penetrant, preferably one high in Nitrogen content, or one that is mixed with a chemical species containing a large proportion of an isotope that has a relatively large fast neutron prompt capture gamma emission cross section, such as Scandium, Vanadium, Manganese or Titanium, that emits a prompt gamma release of a defined energy, to a surface of the material. The surface is then irradiated with a neutron pulse generator and a plurality of beta radiation detectors tuned to the defined energy, are positioned in a regular pattern over the surface of the material to which the mixture is applied to; the plurality of beta radiation detectors respectively providing an output indicative of a reception of the prompt gamma release of the defined energy in an area of the surface viewed by a corresponding one of the beta radiation detectors. The reception is employed to map a characteristic of the defect. In one embodiment the characteristic is the location and length of the defect on the surface. In another embodiment, the characteristic is the depth of the defect on the surface. Preferably, the depth of the defect is determined from the strength of the reception.

In one such embodiment, the mixture is absorbed into the surface by capillary absorption. Desirably, the neutron pulse generator is a neutristor style Neutron Pulse Generator. Preferably, the tuning of the beta radiation detectors is accomplished by placing a high atomic number sacrificial material between the surface and an active portion of the beta radiation detectors to act as an electron radiator. Desirably, the beta radiation detectors are silicon carbide (SiC) detectors with the thickness, distance from the active detector region, and type of material used in the sacrificial layer of the beta radiation detector elected to ensure that mostly the electrons produced by Photoelectric Absorption by the desired emitted prompt gamma radiation energy are completely stopped inside the active region of the SiC detectors. In one such embodiment the sacrificial material is either platinum or tungsten.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENT

Figure 1:
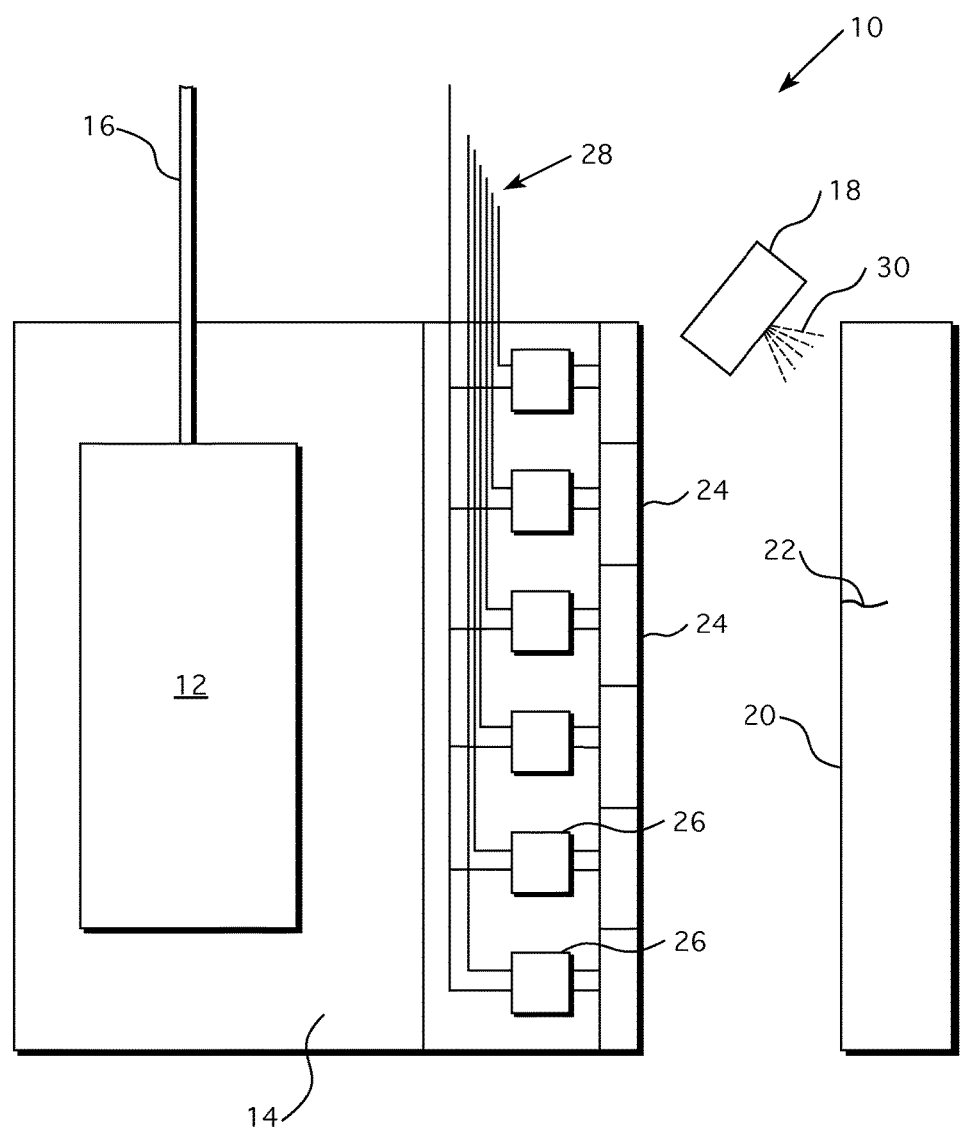
FIG. 1 is a schematic representation of the device layout of this invention.

The operational bases for this invention are founded on a novel combination of dye-penetrant crack detection, prompt neutron gamma radiation detection, and planar Computerized Tomography (CT) techniques. The system also uses a novel SiC tuned gamma intensity detection method and a preamplifier for the very small SiC signal output based on Solid State Vacuum Tube technology. The preferred embodiment is as follows: A non-corrosive crack penetrant, preferably one high in Nitrogen content, or a crack penetrant such as Dynaflux Visible Dye Penetrant available from the Dynaflux Quality Products Company, Cartersville, GA, that is mixed with a chemical species containing a large proportion of an isotope that has a relatively large fast neutron prompt capture gamma emission cross section, such as Scandium, Vanadium, Manganese, or Titanium, is applied at a controlled temperature and pressure, as necessary to ensure the penetrant is in a liquid state when it reaches the surface being inspected. The system described herein has the capability to spray the mixture onto the surface to be examined at high pressure to allow the material to be applied without the system hardware actually touching the surface. A "neutristor" style Neutron Pulse Generator (NPG) assembly, developed by Sandia National Laboratory (Sandia National Laboratory, "Innovation Marketplace", September, 2014, Vol. 1, Issue 3), contained in the measurement assembly is then brought to within an inch of the surface at a radial position known to within 0.1 mm of a fixed surface reference point on the surface by the operator. The NPG assembly is surrounded by an array of specially configured SiC radiation detectors (e.g., 100×100 square of 1 mm² detectors, such as described in U.S. patent application Ser. No. 13/769,401, filed Feb. 18, 2013, entitled Solid State Radiation Detector With Enhanced Gamma Radiation Sensitivity) having positions known to within 0.05 mm of a reference point on the NPG assembly that are tuned to measure primarily the intensity of the Photoelectric Absorption generated electrons produced in material between the gamma radiation emitted from the prompt gamma emitting isotope in the crack penetrant mixture and the active region of the SiC detector as schematically shown in FIG. 1.

Figure 2:
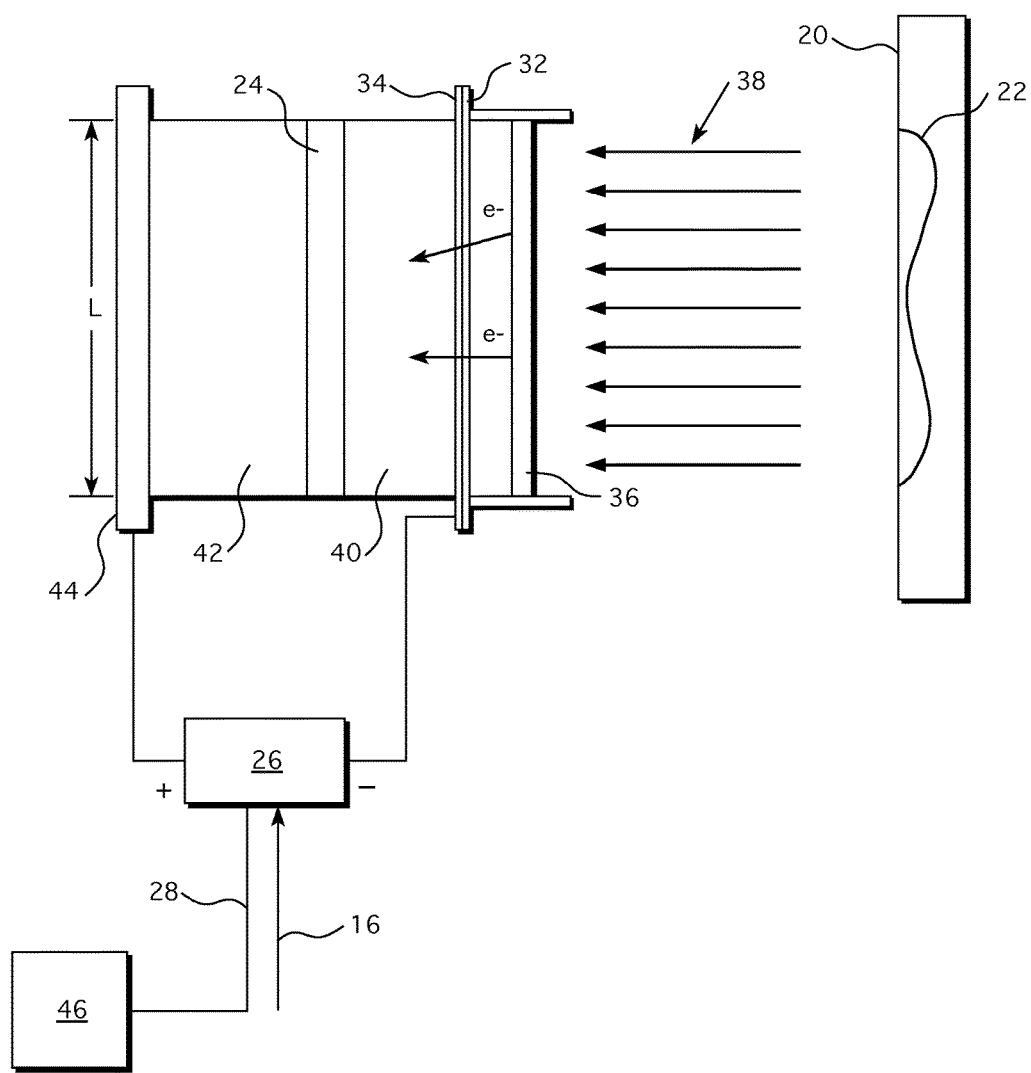
FIG. 2 is a schematic layout of the SiC detector and pre-amplifier used in the SiC detector array of FIG. 1.

The nondestructive examination system 10 of this invention has a spray system 18 that is moveable over the surface 20 of the material to be examined to spray the crack penetrant solution 30 over the surface. The neutron pulse generator 12 emits a stream of pulses that react with the isotope within the crack penetrant solution 30 to emit prompt gamma radiation that is detected by the SiC radiation detectors 24. The outputs of the SiC radiation detectors are fed to the pre-amplifiers 26 with the outputs of the preamplifiers being sent to the processing electronics which interpret the variations in and strength of the received signals to determine the presence of cracks and location, length and depth. The tuning of the SiC beta radiation energy sensitivity is accomplished by placing a high atomic number sacrificial material 36, such as platinum or tungsten, between the surface 20 and the active portion 40 of the SiC detector 24 to act as an electron radiator. The thickness, distance from the active detector region 40, and type of material used in the sacrificial layer 36 of the detector is selected to ensure that mostly the electrons produced by Photoelectric Absorption by the desired emitted prompt gamma radiation energy in the sacrificial layer are completely stopped inside the active region of the SiC detectors. This can be accomplished by those skilled in the art by proper adjustment of the distance between the surfa.ce of the electron radiator 36 and the front face of the SiC Aluminum 32 covering the Schottky interface region 34 so that electrons with less than full gamma energy have little probability of reaching and being stopped in the active volume of the SiC detector. This will ensure that the measured detector output is proportional to the amount of penetrant material in the crack seen by each of the detectors, and therefore to the dimensional properties of the crack. FIG. 2 provides an outline of the SiC detector and associated array geometry.

The SiC detectors 24 receive the prompt gamma radiation 38 through the sacrificial material 36 that convert the prompt gamma radiation to the generation of electrons through Photoelectric Absorption with the distance from the face of the Schottky contact (34) variable to assure all the electrons are captured. The electrons travel through then-doped SiC 40 of approximately 10 µm thick in this example, to the substrate 42 where the electrons are collected by a gold backed ohmic contact 44 and the output current 28 is conveyed to the processing electronics 46 through the preamplifiers 26. The relative measured intensity data obtained from each very small and precisely positioned SiC detector in the detector array after the neutron pulse generator triggers one or more times will be used to determine the dimensional characteristics of the defect. The detector signal output will be input to individual preamplifiers integral to the neutron pulse generator structure utilizing a miniature design like that described in U.S. patent application Ser. No. 14/996,667, filed Jan. 15, 2016, entitled "In-Containment Ex-Core Detector System." The amplified measured detector current signals are then transmitted to a measurement and analysis system located at a convenient location outside the high radiation area. An application specific correlation between the desired measured crack dimensional properties (e.g., depth, width, length) is determined from the SiC detector array geometry and relative measurements of each detector in the array using in-planar CT algorithms.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. A method of nondestructively detecting a structural defect in a surface of an irradiated material comprising the steps of:
    applying a mixture of a noncorrosive crack penetrant including chemical species that have relatively large cross-sections for fast neutron induced prompt gamma emission interactions of a defined energy to the surface of the material to be examined;
    irradiating the surface of the material with a neutron pulse generator;
    positioning a plurality of beta radiation detectors tuned to the defined energy of photo-electrically produced electrons generated in an electron generating window located between an active region of the detector and the surface being examined, in a regular pattern over the surface of the material to which the mixture is applied, the plurality of beta radiation detectors respectively providing an output indicative of a reception of the prompt gamma release of the defined energy in an area of the surface viewed by a corresponding one of the beta radiation detectors; and
    employing the receptions to map a characteristic of the defect.

2. The method of claim 1 wherein the characteristic is a location and length of the defect on the surface.

3. The method of claim 1 wherein the characteristic is a depth of the defect on the surface.

4. The method of claim 3 wherein the depth of the defect is determined from the strength of the reception.

5. The method of claim 1 wherein the mixture is absorbed into the defect by capillary absorption.

6. The method of claim 1 wherein the neutron pulse generator is a neutristor style Neutron Pulse Generator.

7. The method of claim 1 wherein the tuning of the beta radiation detectors is accomplished by placing a high atomic number sacrificial material between the surface being examined and an active portion of the beta radiation deteaors to act as an electron radiator.

8. The method of claim 7 wherein the beta radiation detectors are silicon carbide (SiC) detectors.

9. The method of claim 8 wherein the thickness, distance from the active detector region, and type of material used in the sacrificial layer of the beta radiation detector is selected to ensure that mostly the electrons produced by Photoelectric Absorption by the desired emitted prompt gamma radiation energy are completely stopped inside the active region of the SiC detectors.

10. The method of claim 7 wherein the sacrificial material is either platinum or tungsten.

11. Apparatus for nondestructively detecting and characterizing flaws in the surface of an irradiated material comprising;
    a spray system configured to spray a mixture of a noncorrosive crack penetrant either having a high Nitrogen content, or one that is mixed with a chemical species having a large portion of an isotope that has a relatively large fast neutron prompt capture gamma emission cross section of a defined energy of photoelectric to the surface of the material to be examined;
    a neutron pulse generator configured to irradiate a surface of the material;
    a plurality of beta radiation detectors, tuned to the defined energy of photo-electrically produced electron energy generated in an electron generating window located between an active region of the beta radiation detectors and the surface being examined, the beta radiation detectors positioned in a predetermined pattern over the surface of the material to which the mixture is applied, the plurality of beta radiation detectors respectively providing an output indicative of a reception of the prompt gamma release of the defined energy in an area of the surface viewed by a corresponding one of the beta radiation detectors; and a beta radiation detector output from which the receptions can be employed to map a characteristic of the defect.

12. The apparatus of claim 11 wherein the characteristic is a location and length of the defect on the surface.

13. The apparatus of claim 11 wherein the characteristic is a depth of the defect on the surface.

14. The apparatus of claim 13 wherein the depth of the defect is determined from the strength of the reception.

15. The apparatus of claim 11 wherein the mixture is absorbed into the defect by capillary absorption.

16. The apparatus of claim 11 wherein the neutron pulse generator is a neutristor style Neutron Pulse Generator.

17. The apparatus of claim 11 wherein the beta radiation detectors include a high atomic number sacrificial material between the surface being examined and an active portion of the beta radiation detectors to act as an electron radiator.

18. The apparatus of claim 17 wherein the beta radiation detectors are SiC detectors.

19. The apparatus of claim 18 wherein the thickness, distance from the active detector region, and type of material used in the sacrificial layer of the beta radiation detector is selected to ensure that mostly the electrons produced by Photoelectric Absorption by the desired emitted prompt gamma radiation energy are completely stopped inside the active region of the Sic detectors.

20. The apparatus of claim 17 wherein the sacrificial material is either platinum or tungsten.

* * * * *